US006274334B1

(12) United States Patent
Shelver et al.

(10) Patent No.: US 6,274,334 B1
(45) Date of Patent: Aug. 14, 2001

(54) MONOCLONAL ANTIBODY, CELL LINE AND IMMUNOASSAY FOR RACTOPAMINE

(75) Inventors: Weilin L. Shelver; David J. Smith, both of Fargo, ND (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/615,298

(22) Filed: Jul. 13, 2000

(51) Int. Cl.[7] .................. G01N 33/543; G01N 33/545; G01N 33/563; G01N 33/577; C07K 16/18
(52) U.S. Cl. .................. 435/7.92; 435/7.93; 435/7.95; 435/70.21; 435/452; 435/326; 435/345; 435/810; 435/975; 436/518; 436/528; 436/548; 436/21; 436/815; 436/824; 436/825; 436/901; 436/512; 530/388.9; 530/389.8; 530/391.1; 530/413; 530/807
(58) Field of Search .................. 435/7.92, 7.93, 435/7.95, 70.21, 452, 326, 345, 810, 975; 436/518, 548, 21, 815, 824, 825, 901, 528, 512; 530/388.9, 389.8, 391.1, 413, 807

(56) References Cited

U.S. PATENT DOCUMENTS 5,660,995 * 8/1997 O'Connor ............................ 735/7.93

OTHER PUBLICATIONS

Shelver et al., Jan. 2000. Development of an immunoassay for the β–adrenergic agonist ractopamine. J. Immunoassay 21: 1–23.*
Elliott et al., May 1998. Screening and confirmatory determination of ractopamine residues in calves treated with growth promoting doses of the β–agonist. Analyst 123: 1103–1107.*
Campbell, 1991. Monoclonal Antibody and Immunosensor Technology, Elsevier, Amsterdam, pp. 3–6, 45.*
Shelver et al., 2000b. Production and characterization of a monoclonal antibody against the β–adrenergic agonist ractopamine. J. Agric. Food Chem. 48: 4020–4026, Sep. 2000.*
Haasnoot et al., 1994. Determination of fenoterol and ractopamine in urine by enzyme immunoassay. Analyst 119: 2675–2680, Dec. 1994.*

* cited by examiner

Primary Examiner—Christopher L. Chin
Assistant Examiner—James L. Grun
(74) Attorney, Agent, or Firm—M. Howard Silverstein; Curtis P. Ribando; John D. Fado

(57) ABSTRACT

A hybridoma cell line has been produced for secreting a monoclonal antibody that binds ractopamine and is effective to detect ractopamine levels of about 1 ng/mL or lower. This monoclonal antibody may be used for the detection and quantitative determination of trace amounts of ractopamine in samples, especially in animal tissue, body fluids and feed material.

7 Claims, No Drawings

MONOCLONAL ANTIBODY, CELL LINE AND IMMUNOASSAY FOR RACTOPAMINE

BACKGROUND OF THE INVENTION

1. Field of the Invention

This invention relates to a hybridoma cell line and monoclonal antibody produced therefrom which may be used to detect the β-adrenergic agonist, ractopamine and its metabolites, particularly in animal tissues, excreta, feeds, and in human excretions.

2. Description of the Prior Art

Ractopamine is a phenethanolamine leanness-enhancing agent recently approved as a feed additive for swine by the United States Food and Drug Administration Center for Veterinary Medicine (Federal Register, 65, 4111–4112, 2000; Muirhead, *Feedstuffs*, 72,1, 2000). Hogs administered dietary ractopamine exhibit increased growth rates, feed efficiencies, and greater yields of boneless, closely trimmed retail cuts (Anderson et al., *Fat and cholesterol reduced foods: technologies and strategies*, 43–73, 1990; Stites et al., *J. Anim. Sci.*, 69, 3094–3101, 1991; Watkins et al., *J. Anim. Sci.*, 68, 3588–3595, 1990) relative to untreated control animals. The positive influence of ractopamine hydrochloride on these economically important traits should make the product attractive to swine growers, and perhaps to producers of livestock species for which ractopamine is not approved.

Phenethanolamine β-agonists have a history of being used for off-label purposes by livestock producers (Kuiper et al., *J. Anim. Sci.*, 76, 195–207, 1998; Mitchell et al., *J. Anim. Sci.*, 76, 208–211, 1998) hoping to improve the economics of livestock production; additionally, they have been used extensively by body-builders hoping to modify their phenotypic characteristics (Prather et al., 27, 1118–1121, 1995; Hausmann et al., *Int. J. Legal Med.*, 111:261–264, 1998; Ayotte et al., *J. Toxicol.-Toxin Rev.*, 18, 113–123, 1999). The most commonly abused β-agonist is clenbuterol hydrochloride, a highly potent phenethanolamine (Smith, *J. Anim. Sci.*, 76, 173–194, 1998), that has not been approved for leanness-enhancing effects in livestock or in humans by any regulatory body worldwide.

The presence of drug residues in animal tissues is a concern for food safety, especially when the compound has been used illegally or in a manner proscribed by regulatory officials (off-label use). In an effort to combat the illicit use of β-agonist compounds, regulatory organizations worldwide test animal tissues or excreta for the presence of illicit drugs (Elliott et al., *Vet. Quart.*, 18, 41–44, 1996; Kuiper et al., *J. Anim. Sci.*, 76, 195–207, 1998; Mitchell et al., *J. Anim. Sci.*, 76, 208–211, 1998). For regulatory purposes, both screening and confirmatory assays are used to detect illegal residues. Immunoassays are convenient screening tools used to detect the presence of an analyte in various matrices, and have wide application for determination of the presence of environmental toxins (Sanborn et al., *J. Agric. Food. Chem.*, 46, 2407–2416, 1998), herbicides (Clegg et al., *J. Agric. Food. Chem.*, 47, 5031–5037, 1999), insecticides/pesticides (Wang et al., *J. Agric. Food Chem.*, 47, 3416–3424, 1999; Abad et al., *J. Agric. Food. Chem.*, 47, 2475–2485, 1999), and pharmaceuticals (Stanker et al., *Food Agric. Immuno.*, 10, 121–131, 1998; Brandon et al., *J. Agric. Food Chem.*, 46, 3653–3656, 1998). A successful screening assay should be quick, reliable, and relatively inexpensive. Positive samples from screening assays may then be assayed by more costly and complex instrumental methods such as GC-MS or LC-MS that unequivocally identify the analyte in the sample (eliminating false-positives). However, for screening, immunoassays provide the advantages of high throughput, portability, and sensitivity (detection limits in the ppb range). High sensitivities of immunoassays are particularly desirable for off-label drug monitoring because it may be desirable to detect the analyte even after extended withdrawal periods. Beta-adrenergic agonists immunoassays have been developed for clenbuterol (Yamamoto et al., *J. Immunoassay*, 3: 155–171, 1982), albuterol (salbutamol; Adam et al., *J. Immunoassay*, 11, 329–345, 1990), fenoterol (Haasnoot et al., *Analyst*, 119, 2675–2680, 1994), as well as ractopamine (Haasnoot et al., *Analyst*, 119, 2675–2680, 1994; Elliott et al., *Analyst*, 123, 1103–1107, 1998; Shelver et al., *J. Immunoassay*, 21, 1–23, 2000). Currently available immunoassay kits cross-react poorly with ractopamine (Wicker et al., *Analyst*, 120, 2879–2881, 1995), and the immunoassay previously reported for ractopamine was generated from polyclonal antibodies. Development of an immunoassay based on a monoclonal antibody is advantageous, relative to a polyclonal based immunoassay because a continuous supply of a homogeneous antibody can be assured, eliminating the batch-to-batch differences commonly encountered with polyclonal antibodies.

SUMMARY OF THE INVENTION

We have now discovered a hybridoma cell line designated 5G10 that produces and secretes a monoclonal antibody toward the β-adrenergic agonist ractopamine hydrochloride {(1R*, 3R*), (1R*, 3S*)-4-hydroxy-β-[[[3-(4-hydroxyphenyl)-1-methylpropyl]amino]methyl]-benzenemethanol hydrochloride}. This cell line secretes antibody with isotype IgGlκ shown to be useful for the development of an immunoassay. The antibody is specific for racemic ractopamine, and also binds stereoselectively with the (1R,3R) isomer which is responsible for conferring biological activity to the molecule. Phenethanolamine β-agonists show low cross-reactivity.

The monoclonal antibody of this invention may be incorporated into kits for the detection and quantitative determination of low levels of ractopamine in samples, especially in human and animal tissue, body fluids and excreta, and also in feed material. Detection of ractopamine in sample materials is accomplished using immunosorbent assay procedures conventional in the art.

It is an object of this invention to provide a hybridoma cell line that produces and secretes a high affinity monoclonal antibody which is specific for ractopamine, stereoselective for the (1R,3R) isomer, and effective for detecting and quantifying ractopamine in sample materials at very low levels.

Another object of this invention is to provide immunoassay methods for determining off-label and illegal use of ractopamine and for detecting levels of ractopamine exceeding tolerance limits in samples.

A further object is to provide kits useful for the assay of ractopamine based on the monoclonal antibody described herein.

Yet another object is to provide a method for recovering or removing ractopamine from any material such as by affinity purification.

Other objects and advantages of this invention will become readily apparent from the ensuing description.

DEPOSIT OF BIOLOGICAL MATERIAL

The cloned hybridoma cell line 5G10 was deposited on Jun. 20, 2000, under the conditions of the Budapest Treaty with the American Type Culture Collection, 10801 University Blvd., Manassas, Va. 20110-2209, USA, and has been assigned number ATCC PTA-2103.

DETAILED DESCRIPTION OF THE INVENTION

In accordance with this invention we have created a hybridoma cell line that produces a monoclonal antibody that binds ractopamine, has an unexpectedly high stereoselectivity for the (1R,3R) isomer and is effective for detecting and quantifying very low levels of the β-agonist. The monoclonal antibody of the invention is capable of detecting ractopamine levels of 0.5 ng/mL [at 80% $B/B_0$ ($IC_{20}$)] in competitive inhibition ELISA.

Preparation of the hybridomas may be accomplished using conventional techniques such as described by Kohler and Milstein (Nature, 256:495–497, 1975), Koprowski et al. (U.S. Pat. No. 4,196,265) or Wands (U.S. Pat. No. 4,271,145), the contents of each of which are incorporated by reference herein. Generally, the process of preparation comprises the steps of immunizing an animal with the antigen of interest, recovering splenocytes or lymphocytes from the animal, fusing the splenocytes or lymphocytes with continuously replicating myeloma cells to produce hybrid cells, and screening the resultant hybrid cells for the production of antibodies to the antigen. However, because ractopamine is a relatively small molecule, it is itself incapable of stimulating the immune system to produce antibodies. To render the compound immunogenic, it must first be conjugated to an immunogenic carrier in such a manner that the resultant immunogen is capable of stimulating the immune system of an animal to produce specific antibodies that are capable of binding the unconjugated ractopamine.

The structure of ractopamine is as follows:

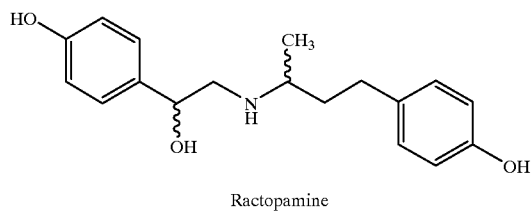

Ractopamine

This compound is rendered immunogenic by coupling it to an immunogenic carrier by the following procedure.

Immunogen. The immunizing agent is constructed by covalently conjugating ractopamine to an immunogenic carrier protein, preferably by means of a crosslinker, such as a glutarate moiety. Immunogenic carriers are defined herein as any compound to which ractopamine may be attached to render it immunogenic. Suitable carriers are well known and may be readily determined by the skilled practitioner in the art. Without being limited thereto, preferred carriers include proteins such as keyhole limpet hemocyanin (KLH), bovine serum albumin (BSA), ovalbumin (OVA) and human thyroglobulin. The function of the crosslinker is to introduce into the molecule a spacer of sufficient size to prevent the carrier protein from masking the ractopamine molecule.

Inmunization. To generate antibody-producing splenocytes or lymphocytes, an immunizing preparation comprising the antigen (ractopamine-carrier conjugate) is injected into an immunologically competent animal. The preparation may also contain other proteins, although pure or substantially pure compositions of the conjugate in a pharmaceutically acceptable carrier are preferred.

Without being limited thereto, rats and particularly mice are preferred hosts for raising antibodies because of ease of handling. BALB/c mice are most commonly used. Preparation of hybridomas using splenocytes from these animals fused to any of a variety of myeloma cell lines, such as SP2/0, is well-known in the literature.

Certain aspects of the immunization protocol are critical to production of high affinity monoclonal antibodies. It is important that the injection schedule be sufficient to allow for maturation of the immune response in the animal. Preferably, a series comprising an initial injection followed by 3–4 boosters at approximately 30-day intervals should be given prior to fusion. The dose of antigen injected should, of course, be sufficient to stimulate the immune system. Extrapolating from the success of employing 100 μg conjugate per injection in the Examples below, it is anticipated that any reasonable amount in excess of about 25 μg per injection would also be effective. Typically, the antigen is suspended in a physiological vehicle, such as isotonic saline or PBS buffer. In accordance with a preferred embodiment, an adjuvant may be incorporated into the immunizing preparation for enhanced stimulation of the immune system, particularly for the first 1–2 or 1–3 injections. A variety of adjuvants which are conventional in the art may be used herein, although Freund's or RIBI adjuvants are preferred. The route of injection is typically intraperitoneally, though other routes would also likely be effective in inducing an immune response.

Hybridization. Splenocytes or lymphocytes recovered from the immunized animal are fused with continuously replicating tumor cells, such as myeloma or lymphoma cells, cultured, and hybridoma cells selected using techniques conventional in the art. Many continuously replicating tumor cell lines are available which may be used as fusion partners with the splenocytes. Without being limited thereto, preferred myeloma cells include P3, NS1, K653, and particularly SP2/OAg14.

Fusion and culture of the cells can be performed using conventional techniques. In accordance with one well known effective procedure, the splenocytes and myeloma cells are fused by exposure to polyethylene glycol. Hybrid cells are selected by culture in hypoxanthine-aminopterin-thymidine (HAT) medium, whereby unfused myeloma cells are killed by HAT and splenocytes die out, leaving only the hybrid cells. The resultant hybridomas are then grown in RPMI or other suitable culture medium and assayed for antibody production.

Screening. Samples of the supernatant culture fluid from the hybridomas are screened for antibodies to ractopamine. While the supernatants may be screened using a plurality of techniques such as RIA and ELISA, in accordance with the preferred embodiment of the invention, an indirect ELISA is employed. Generally, solid substrates, such as beads or the wells of a microtiter plate, which are coated with the antigen or antigen conjugate, are used to bind anti-ractopamine antibody in the supernatants. A preferred coating is ractopamine-glutarate-BSA. Detection of bound antibody may be accomplished by addition of enzyme-labeled anti-immunoglobulin antibodies followed by enzyme substrate. Horse radish peroxidase and its substrate, 2,2'-azinobis-3-ethylbenthiazoline-sulfonic acid (ABTS) are preferred enzyme/substrate labels. However, it is understood that other enzyme/substrate labels or non-enzyme labels such as radiolabels or chromophores may also be used.

Cloning. Cloning of hybridomas which are positive for desired antibody production can be carried out as soon as they are detected by any method known in the art. Hybridomas having a positive response in the ELISA screen are preferably expanded and subcloned one or more times by limiting dilution to assure monoclonality.

The supernatant culture fluid from the cloned hybridomas may also be screened to select for those producing antibodies having a high affinity for ractopamine. Affinity may be measured using a variety of well known techniques, such as ELISA, RIA or equilibrium dialysis using labelled ractopamine. Competitive indirect ELISA (CI-ELISA) is preferred, and is conducted at a final antibody concentration (dilution from tissue culture supernatant) to give 50% of maximal binding to a ractopamine coated substrate or assay well. In accordance with this embodiment, the antibody containing supernatant is added to a ractopamine conjugate-coated solid substrate such as the wells of an assay plate, together with a range of concentrations of free ractopamine as a competitor. Following incubation and washing, bound antibody in the wells is determined in the same manner as the indirect-ELISA. Percent inhibition may be calculated as $(1-B/B_0) \times 100$ where B is the optical density (OD) of a well with a competitor and $B_0$ is the mean OD of the wells without competitor (control). The relative affinity of the antibodies may be accurately measured as the concentration of free ractopamine added to the wells that resulted in at least 20% inhibition ($IC_{20}$) of the control activity. However, for even greater accuracy, the affinity may be alternatively measured at 50% inhibition ($IC_{50}$).

Antibody Production and Purification. Once hybridomas producing and secreting the desired anti-ractopamine antibodies are identified, large quantities of the antibody may be produced in tissue culture using well-known techniques. Alternatively, antibody may be produced within host animals, such as by ascites formation in syngenic mice. Monoclonal antibodies so produced may be purified, for example, by affinity chromatography on a protein A or G resin, or using ractopamine bound to a resin.

Uses of Monoclonal Antibody. The monoclonal antibodies produced in accordance with this invention possess very high affinity for ractopamine, allowing the determination of the β-agonist at very low levels of less than about 1 ng/mL, and even at levels of about 0.5 ng/mL or lower.

These antibodies may be used to detect and quantify ractopamine in unknown samples using well known immunosorbent assay procedures including but not limited to RIA or ELISA. A competitive inhibition ELISA similar to that used to screen the hybridomas is preferred. In this assay, a sample to be analyzed is incubated with the monoclonal antibody for ractopamine and a solid substrate coated with ractopamine conjugate. It is preferred to use a conjugate having a protein different from that used in the immunization protocol in order to avoid detection of antibodies to the protein carrier. After incubation, the solid phase is drained and washed, bound antibody on the coating antigen is detected, and percent inhibition is calculated as described earlier. The concentration of ractopamine in the sample may then be determined by reference to a standard curve constructed from assays using known levels of ractopamine.

In one alternative embodiment, ractopamine may be determined by a competition ELISA such as described in Brandon et al. (U.S. Pat. No. 5,053,327, the contents of which are herein incorporated by reference) using the monoclonal antibody of the invention attached to a solid support. For example, the anti-ractopamine antibody may be immobilized on a bead or in a microtiter well. The unknown sample to be analyzed (or analytical standards of ractopamine) are then added together with enzyme-labeled, or radio-labeled, ractopamine. The amount of labeled ractopamine bound to the antibody is then measured, using a substrate when the label is an enzyme. The amount of ractopamine in the sample is inversely proportional to the amount of bound labeled ractopamine. In another embodiment, the monoclonal antibody may be attached to a solid support for use in conventional double-antibody sandwich ELISA procedures.

An assay using the antibodies of the invention would have the advantages of being more specific than a microbiological assay, and more rapid and less expensive than HPLC. It can be incorporated into a residue monitoring program as a rapid initial screen to eliminate samples that do not contain violative levels of ractopamine. Therefore, use of this method to detect ractopamine in edible tissues or excretions has the potential to increase sample throughput and to decrease costs associated with sample analyses.

With any of the above-described assay formats, the monoclonal antibodies of the invention may be incorporated into kits alone, or preferably together with any other necessary reagents. Such a kit for use herein comprises a first container comprising the monoclonal antibody, a second container comprising a detection reagent effective for detecting bound antibody, and ractopamine conjugate bound to a solid support.

Determination of ractopamine in animal tissue samples, body fluids, excretions or feeds may be conducted using the above-described assay with minimal sample preparation and without extensive extraction procedures. Samples need only be homogenized in buffer, such as Tris-NaCl (pH 7.5) or digested in alkali and neutralized. The suspended sample is then centrifuged, and the liquid phase is recovered for use in the immunoassay. Although any animal tissue may be analyzed, the assay is particularly valuable for the determination of ractopamine in edible tissues. Tissue for analysis in accordance with the invention may originate from virtually any animal. Without being limited thereto, the analysis of tissue samples from domestic animals, including equines, bovines, ovines, poultry and swine are encompassed by this invention.

Several applications for testing animals are envisioned. For the determination of off-label ractopamine use, animal tissues such as eyes, hair, muscle, adipose tissue, liver, or kidney may be tested for the presence of ractopamine and its metabolites. For such an application, the sensitivity of the assay would be maximized to detect low levels of ractopamine. In animals not destined for slaughter, such as show animals, racing animals, milk animals, or breeding animals, it is envisioned that urine or saliva could be tested for the presence of ractopamine. By necessity, such an assay would require great sensitivity. In species for which no regulatory approval of ractopamine has been granted, positive results obtained after testing tissues or excreta would indicate that off-label ractopamine use has occurred. Because the misuse of β-agonists by human athletes and body builders has been documented on numerous occasions, it is envisioned that a sensitive assay for ractopamine using the antibodies described herein would also be used to determine illegal ractopamine use in humans.

The monoclonal antibodies of the invention also have application by regulatory bodies having an interest in determining ractopamine levels in tissues of species for which ractopamine approval has been granted. In such a scenario, assays would be constructed so that the limit of detection corresponds to a regulatory action level such as a tolerance. For example, assays could be constructed so that positive results would be obtained only when the tolerance of ractopamine (FDA, Freedom of Information Summary, NADA no. 140–863, page 61, 2000) in swine liver (150 ppb) and muscle (50 ppb) were exceeded.

Another application of the monoclonal antibodies is affinity purification of ractopamine. The antibodies may be bound to a matrix, column, or other support using well-known techniques and used to recover or remove ractopamine from any desired material. Alternatively, the antibodies may be incorporated into sensors such as solid phase electronic devices for detection of ractopamine in sample materials.

In an alternate embodiment of the invention, it is understood that antibody fragments having the epitope for recognizing (or binding) the ractopamine analyte could be substituted for the intact IgG for the several end-use applications described above. In illustration, the Fab monovalent fragment can be generated by digestion of the IgG with papain and the $(Fab')_2$ bivalent fragment can be generated by digestion of the IgG with pepsin. Also, the sFv (single chain variable fragment) can be used for the same purpose as the intact IgG for binding ractopamine.

The following examples are intended only to further illustrate the invention and are not intended to limit the scope of the invention which is defined by the claims.

EXAMPLE 1

Immunogen Preparation (Hapten Synthesis)

Synthesis of Ractopamine-hemiglutarate

Ractopamine HCl (34 mg; 0.1 mmole), with a trace amount ($3 \times 10^5$ dpm) of [$^{14}$C]ractopamine, was reacted with 12 mg (0.1 mmole) of glutarate anhydride in the presence of 2 ml pyridine. The reaction was stirred overnight at room temperature. The extent of the reaction was ascertained using silica gel thin layer chromatography (TLC) developed by 90% $CH_2Cl_2$:10% methanolic $NH_4OH$ (10%). The plates were scanned for $^{14}$C activity using a TLC scanner (BIOSCAN®, Inc. Washington, D.C., USA). After the reaction was complete, the pyridine was evaporated under a stream of nitrogen and the ractopamine hemiglutarate was used for carrier protein conjugation.

Synthesis of Immunogen

Immunogen was formed by dissolving ractopamine hemiglutarate (0.1 mmole) in 4 ml of DMF:1,4-dioxane (1:1) and adding 26.2 µL (0.11 mmole) of tributylamine. The mixture was stirred on ice for 10 min, isobutylchloroformate (0.11 mmole) was added, and the reaction was brought to room temperature and stirred for 1 hr. The mixture was added dropwise to an ice-cold protein solution (100 mg BSA, or 50 mg KLH dissolved in 0.1 M sodium borate, pH 8.5). The resulting solution was brought to room temperature and allowed to react overnight. The final solution was dialyzed against several changes of phosphate buffered saline (PBS) (each liter contained 8 g NaCl, 0.2 g KCl, 1.44 g $Na_2HPO_4$, 0.24 g $KH_2PO_4$ in $H_2O$) and the conjugation ratios were checked by measuring the radioactivity incorporated in the protein or by comparing the apparent molecular weight of conjugate to carrier protein on 10% SDS-PAGE.

EXAMPLE 2

Hybridoma and Monoclonal Antibody Production

Preparation of Mice

Four female BALB/c mice, 8 weeks old, were initially immunized by intraperitoneal injection with 100 µg of ractopamine-glutarate-KLH as prepared in EXAMPLE 1 mixed with complete Freund's adjuvant. Four booster immunizations were administered at 30-day intervals using antigen emulsified with incomplete Freund's adjuvant. Blood was collected 10 to 14 days after the last booster immunization in order to check for antibody titers. Titers were checked using both indirect ELISA and competitive ELISA that employed ractopamine-glutarate-BSA as the coating antigen and racemic ractopamine as competitor. Two mice that produced high titers (1:16,000) after the $4^{th}$ boost, and showed competition toward ractopamine, were used for fusion experiments. Four days prior to splenocyte harvest, mice were injected with 50 µg of antigen through their tail veins.

Monoclonal Antibody Generation

Murine myeloma cells Sp2/0Ag14 were grown in RPMI1640 supplemented with 15% fetal bovine serum, 100 units/mL penicillin, 100 µg/mL streptomycin, and 0.25 µg/mL of amphotericin B (designated as complete media). The culture media supernatant from the Sp2/0Ag14 was used as the conditioned media and replaced feeder cells in the fusion and cloning experiment. Splenocytes were fused with Sp2/0Ag14 murine myeloma cells using fusion, selection, cloning, expansion, and ascites generation procedures described by Barrett (*Antibody Techniques*, pp 71–102, 1994). Briefly, splenocytes from two mice were harvested and fused with Sp2/0Ag14 cells by PEG 1500. Fused cells were suspended in complete media supplemented with 30% conditioned media and plated into a total of 13 96-well cell culture plates. The HAT selection was performed from days 3 to 14 post fusion by supplementing 10 µM sodium hypoxanthine, 0.4 µM aminopterine, and 16 µM thymidine to the complete media. After HAT selection, microscopic inspection revealed cell growth in 137 out of 1248 wells.

Two weeks after cell fusion, hybridomas were screened for their ability to produce antibodies that recognize ractopamine using indirect ELISA. A non-competitive and a competitive indirect ELISA were performed simultaneously using ractopamine-glutarate-BSA as coating antigen. The coating antigen was prepared by linking the hapten (ractopamine hemiglutarate) to bovine serum albumin (BSA) as described above for synthesizing the KLH conjugate, except that 100 mg BSA was substituted for the 50 mg KLH. The use of different carrier proteins for immunization and coating antigen assures the assay is not confounded by recognition of the protein portion of the immunogen. The protocol of ELISA procedure is essentially the same as described, below, for the specificity determination.

Hybridoma Expansion

Of the 137 active wells, 23 tested positive in ELISA towards the ractopamine hapten. Hybridomas that showed continuous growth, the ability to withstand liquid nitrogen freezing and subsequent thawing, and showed the ability to continuously secrete antibody able to compete for ractopamine were selected for cloning. These hybridomas were expanded into 24-well cell culture plates followed by culturing in T-flasks, and cloned twice using a limiting dilution technique. Four hybridomas, namely 4B7, 5G10, 7D12, and 13B2, were chosen for ascites generation. Mice were primed with pristane (ip) 12 days prior to the injection of $1 \times 10^6$ (4B7, 5G10, 13B2) or $5 \times 10^5$ (7D12) cells. Ascites were collected one-week after injection of the cloned cells and were frozen at –20° C. until used. Hybridomas were pelleted by centrifuging at 400 g and were re-suspended into DMSO freeze medium and cryopreserved in liquid nitrogen.

Antibody sensitivities of the selected clones, based on their ability to compete with racemic ractopamine, were 5G10>13B2>4B7>7D12. Because antibody produced from clone 5G10 was the most sensitive towards ractopamine, it was chosen for further evaluation of antibody specificity and subsequent immunoassay development.

Monoclonal Antibody Isotyping

Antibody type was determined following the manufacture's instructions supplied with a commercial kit (Pierce, Rockford, Ill.). Briefly, 50 µL/well of a 5 µg/mL ractopamine-glutarate-BSA solution was coated on a 96-well ELISA plate in 50 mM sodium bicarbonate buffer (pH 9.6) and the plate was kept overnight at room temperature. After the removal of coating antigen, the plate was blocked with 125 µL/well of 0.5% BSA at 37° C. for one hour. The plate was washed four times with PBST, 50 µL of ascites 1:1000 was added to each well, and the plate incubated at 37° C. for one hour. After washing the plate four times with PBST, subclass rabbit anti-mouse immunoglobulins (IgG) were added to each well and incubated at 37° C. for one hour. The plate was washed, horseradish peroxidase conjugated goat anti-rabbit IgG was added, and the plate incubated at 37° C. for one hour. After washing the plate, ABTS (2,2'-Azinobis(3-ethylbenthiazoline-sulfonic acid) substrate solution 100 µL/well was added, incubated 20 minutes at room temperature, and the plates were read at 415 nm. The isotypes of the selected hybridomas are as follows: 4B7:IgMλ; 5G10:IgGlκ; 7D12:IgGlκ; and 13B2:IgGlκ.

Antibody Specificity Determination

The checkerboard method was used to determine the optimum amount of coating antigen-ractopamine-glutarate-BSA (0.1 to 1 µg/well), primary antibody (1:4000 to 1:14,000), and secondary antibody (1:5000 to 1:50,000) required for the indirect competition ELISA. After optimization, a competitive ELISA procedure was used to determine the inhibition concentration ($IC_{50}$) for ractopamine and structurally related compounds described below. Ninety-six well flat bottom ELISA plates were coated with 500 ng/well of ractopamine-glutarate-BSA in 50 mM bicarbonate buffer, pH 9.6, and allowed to shake for 2 hours using an orbital shaker after which the plates were washed 5 times with PBST. Excess binding sites in each well were blocked by incubating with a 1% solution of Teleostean® cold water fish gelatin for 1 hour after which each well was washed 5 times with PBST. Primary antibody (5G10), diluted to 1:14,000, was added (50 µL/well) in the presence of competitor (100 µL/well) and was incubated for 1.5 hours. Competitors were incubated at concentrations of 0, 0.1, 0.5, 1, 5, 10, 50, 100, 500, 1000, 5000, and 10,000 ng/mL. A racemic ractopamine calibration curve was used in every experiment as a quality control. Washing wells five times with PBST terminated the reactions. Goat anti-mouse IgG peroxidase conjugate, diluted 1:50,000 (100 µL/well), was incubated for 1 hour. A TMB substrate solution was used during color development (30 min); the color development was stopped by adding 50 µL/well of 2 N $H_2SO_4$. All incubations were conducted at 37° C. The plates were read at 450 nm and the data analyzed using a four-parameter logistic equation for the competitors that produced competition curves.

Table 1 shows the selectivity of the antibody produced by hybridoma 5G10. In absolute measures, the antibody was most selective toward the (1R,3R) stereoisomer of ractopamine with a cross reactivity of 489% relative to the racemic mixture. The unique stereospecificity of the invention is of importance because the (1R,3R) stereoisomer of ractopamine is the isomer of ractopamine which confers biological activity to the molecule (E. A. Ricke et al., *J. Anim. Sci.* 77:701–707, 1999; N. W. Shappell et al., *J. Anim. Sci.* 78:699–708, 2000). With the α-methyl group on the butylamine moiety in the (S) configuration (i.e., 1R,3S ractopamine), antibody binding decreased by a factor of 100 indicating the stereochemical configuration at this carbon was critical to efficient binding. Although the stereochemical orientation of the β-hydroxyl group (the benzylic alcohol) affected antibody binding, its effect was less pronounced than that of the α-methyl group as confirmed by the $IC_{50}$ values of R-des-OH-ractopamine and S-des-OH-ractopamine (both lacking the β-hydroxyl) shown in Table 1.

Data obtained with racemic dobutamine, a structural isomer of ractopamine (lacking the benzilic hydroxyl and substituting a catechol for the ethanolamine-phenol of ractopamine), confirms observations made with des-hydroxy ractopamine regarding the importance of the N-alkyl group in antibody binding.

The importance of ractopamine's phenolic groups in antibody binding was confirmed in competition assays using a series of methylated analogs (LY99418; LY227274; and LY227273) as well as synthetic ractopamine-glucuronide metabolites (see Table 1). The free N-alkyl phenolic group on LY227273 accounts for the low $IC_{50}$ (2.6 ng/mL) as compared to significantly higher $IC_{50}$ values of 233 and 250 ng/mL for the other two analogs (LY99418 and LY227274, respectively) that are methoxylated at this position.

The specificity of the antibody for the free N-alkyl phenol was unequivocally confirmed using binding experiments with synthetic ractopamine glucuronides. These compounds were synthesized according to Smith et al. (*Drug Metab. Dispos.* 21: 624–633, 1993) and the diastereoisomers were purified using liquid chromatography. Ractopamine glucuronide A [composed of 66 and 33% of the (1S,3R) and (1R,3S), ractopamine respectively] and ractopamine glucuronide B [composed of equal quantities of the (1R,3R) and (1S,3S) stereoisomers] were both conjugated to the N-alkyl phenol of ractopamine, whereas ractopamine glucuronide C [composed of 27%, 19%, 28%, and 26% of the (1R,3R), (1S,3R), (1S,3S), and (1R,3S) ractopamine stereoisomers, respectively] was conjugated to the ethanolamine phenol. Relative to the (1R,3R) stereoisomer of ractopamine, ractopamine glucuronides A and B were over 100 times poorer ligands for the monoclonal antibody. In contrast, ractopamine glucuronide C bound to the antibody with an affinity almost as great as (1R,3R) ractopamine (see Table I). The fact that the antibody is extremely sensitive to ractopamine glucuronide C is an excellent property for off-label screening purposes because this metabolite has been identified in various species dosed experimentally with ractopamine HCl. Thus, it is highly likely that animals dosed with ractopamine in an off-label manner can be tested and the presence of either parent ractopamine or its metabolite detected.

As the N-alkyl substituents of β-agonists diverge from that of ractopamine, the antibody binding decreases substantially (Table 1). Ritodrine and fenoterol, which have N-β-(4-hydroxyphenyl)-ethyl substituents, rather than ractopamine's N-γ-(4-hydroxyphenyl)-propyl substituent, display binding affinities 30 to 1000 times lower than racemic ractopamine. With further divergence in structure from ractopamine, antibody binding becomes negligible or nearly so. The β-agonist most commonly associated with illegal use, clenbuterol, did not cross react with the 5G10 antibody.

EXAMPLE 3

Matrix Effects, and Assay Parameter Determinations

Ractopamine (0, 0.1, 0.5, 1, 5, 10, 50, 100, 500, 1000, 5000, and 10,000 ng/mL) was added to bovine urine samples diluted 1:2, 1:5, 1:10, and 1:20 with PBST. Urine was collected from a Holstein cow that had not received any ractopamine treatment. Immunoassays in diluted matrices were run according to the procedure described in Example 2. The resulting competition data were fit to a four-parameter logistic equation using the program manager provided by the plate reader (Bio-Rad® Laboratories, Hercules, Calif.) and the $IC_{50}$ values were determined. The $IC_{50}$ and $B_0$ from each diluted urine curve were compared with $IC_{50}$ and $B_0$ values generated from the PBST standard curve. Ractopamine in a 1:10 urine dilution at concentrations of 1, 5, 10, 20 ng/mL were divided and stored at −20° C. until used. For determination of intra-assay variation, each concentration of the spiked urine samples was pipetted into 12 wells, along with the appropriate standard curve (0 to 10 μg/mL, 12 levels) and the data processed using the spiked samples as replicated unknowns. Inter-assay variation was determined in a similar manner on five separate days with duplicate wells for each level of spiked sample.

Results from intra- and inter-assay experiments were used to test the precision and accuracy. The linear range of the percentage $B/B_0$ vs. log ractopamine concentration competition curve generated in PBST was 0.8 to 12 ng/mL. The limit of detection for racemic ractopamine using a cutoff criteria of 80% $B/B_0$ was 0.5 ng/mL. Although in most cases, the affinity constants for monoclonal antibodies are generally lower than for polyclonal antibodies, the 5G10 monoclonal antibody had an affinity for racemic ractopamine comparable to polyclonal antibodies generated from rabbits ($IC_{50}$ 2.7 vs 4.2 ng/mL). The major difference is that the 5G10 monoclonal antibody is more selective than the polyclonal antibody. In addition, the monoclonal antibody had excellent sensitivity towards the (1R,3R) stereoisomer of ractopamine, having a detection limit of 0.1 ng/mL in PBST.

Bovine urine was used for the determination of the immunoassay's ruggedness and its potential application in detecting off-label usage of racemic ractopamine. The mean $B_0$ (antibody binding with no competitor present) for urine dilutions 1:2, 1:5, 1:10, and 1:20, had absorbances of 0.17, 0.34, 0.63, and 0.95 (n=3 per dilution), respectively, compared with 1.27 for antibody in PBST. The $IC_{50}$ values, using racemic ractopamine as the competitor, were 11.58, 4.62, 3.16, 3.02 ng/mL compared with 2.49 for buffer. Because urine diluted 1:10 caused only a small effect on the assay based on the deviation of the $IC_{50}$ from PBST, a 1:10 dilution was used to generate the precision and accuracy data. Table 2 indicates that the intra-assay variation had a coefficient of variation below 6%. Recoveries were within 20% of theoretical values indicating acceptable accuracy. Coefficient of variation values ranging from 16% to 38% were obtained for the inter-assay variation experiments. As might be expected, variation was greatest for the low concentration (1 ng/mL) samples. These results demonstrate that the immunoassay could be used with no sample preparation (no organic solvent extraction is needed) other than simple dilution.

EXAMPLE 4

Immunoaffinity Column (IAC) Generation and IAC Usage for Ractopamine and Ractopamine Metabolites Isolation Ten milliliters of acites containing ractopamine antibody were diluted with 0.1 M acetate buffer (1:3) and centrifuged. The diluted ascites was passed through a protein-G column and non-bound material was washed off with 0.1 M acetate buffer, pH 5.0, followed by 0.1 M glycine, pH 2.8 to elute the IgG. The protein concentration was determined by $OD_{280}$ and confirmed by the method of Bradford. The IgG purity was confirmed by 10% SDS-PAGE. Purified IgG was conjugated with CNBr-Sepharose according to a standard procedure. Five milligrams of IgG was conjugated with 1 mL of CNBr-Sepharose to produce the immunoaffinity beads. The immunoaffinity beads were packed to a screening column. A solution containing approximately equal amounts of C-14 labeled ractopamine and ractopamine glucuronide was applied to the column. The column was subsequently eluted with 0, 10%, 30%, 50%, 70% and 100% MeOH; eluants were collected and counted for C-14 activity to verify recoveries. The radioactivity was mainly in the 50% and 100% MeOH fractions and only low levels of radioactivity were recovered in the 0 and 10% MeOH column washes. Thus, the ractopamine IAC retained both ractopamine and ractopamine metabolites, and has the potential to be used for the rapid isolation of ractopamine and (or) ractopamine metabolites from solution. Such a technique would have wide application in the preparation of samples undergoing a ractopamine confirmatory assay.

EXAMPLE 5

Generation of Fab Fragment

Purified IgG isolated by sodium sulfate precipitation or a protein G column is digested with 2% papain in the presence of reducing agents such as cysteine, dithiothreitol, or β-mercaptoethanol, and the progress is monitored by SDS-PAGE. After dialysis into a suitable buffer such as PBS, an Fab fragment can be isolated by ion-exchange or affinity chromatography and the purity confirmed by SDS-PAGE. The resultant Fab fragment will have a molecular weight of approximately 50 KD, which is approximately ⅓ the molecular weight of the parent IgG. It is monovalent compared to the IgG, which is bivalent. (McClurkan, et al., *J. Pharm. Exp. Ther.*, 266, 1439–1445, 1993, herein incorporated by reference).

EXAMPLE 6

Generation of (Fab')$_2$ Fragment

Purified IgG isolated by sodium sulfate precipitation or a protein G column is digested with 2% pepsin in the presence of reducing agents such as cysteine, dithiothreitol, or β-mercaptoethanol, and the progress is monitored by SDS-PAGE (Kilchherr et al., *J. Immuno.*, 138, 849–855, 1987). After dialysis into a suitable buffer such as PBS, an (Fab')$_2$ fragment can be isolated by ion-exchange or affinity chromatography and the purity confirmed by SDS-PAGE. The resultant (Fab')$_2$ fragment will have a molecular weight of approximately 110 KD, which is approximately ⅔ the molecular weight of the parent IgG and has the same bivalency of the parent IgG.

TABLE 1

$IC_{50}$ and percentage cross-reactivities of ractopamine, ractopamine stereoisomers, ractopamine metabolites, ractopamine analogs, and selected phenethanolamine β-agonists.

| Compound | $IC_{50}$[a] ng/mL | Cross-reactivity[b] (%) |
|---|---|---|
| Ractopamine (racemic) | 2.69 ± 0.36 | 100 |
| (1R, 3R)-ractopamine | 0.55 ± 0.09 | 489 |

TABLE 1-continued

IC$_{50}$ and percentage cross-reactivities of ractopamine, ractopamine stereoisomers, ractopamine metabolites, ractopamine analogs, and selected phenethanolamine β-agonists.

| Compound | IC$_{50}$[a] ng/mL | Cross-reactivity[b] (%) |
|---|---|---|
| (1R, 3S)-ractopamine | 291 ± 32 | 0.9 |
| (1S, 3R)-ractopamine | 2.00 ± 0.37 | 134 |
| (1S, 3S)-ractopamine | 140 ± 23 | 1.9 |
| R-des-OH-ractopamine | 1.59 ± 0.09 | 169 |
| S-des-OH-ractopamine | 25.2 ± 1.9 | 10.7 |
| Dobutamine | 50.3 ± 8.1 | 5.3 |
| LY99418 | 232 ± 26 | 1.2 |
| LY227274 | 250 ± 40 | 1.1 |
| LY227273 | 2.62 ± 0.08 | 103 |
| Ractopamine glucuronide A | 263 ± 20 | 1 |
| Ractopamine glucuronide B | 87.8 ± 5.0 | 3.1 |
| Ractopamine glucuronide C | 0.70 ± 0.04 | 384 |
| Ritodrine | 73.8 ± 4.4 | 3.6 |
| Fenoterol | 2682 ± 350 | 0.1 |
| Bamethane | 831 ± 11 | 0.3 |
| Isoxsuprine | 1391 ± 127 | 0.2 |
| Salmeterol | 1519 ± 116 | 0.2 |
| Clenbuterol[c] | — | <0.1 |
| Salbutamol[c] | — | <0.1 |

[a]Data represent means of three separate experiments run on three different days. The value for racemic ractopamine represents the average of 15 experiments performed over a three month period.
[b]Percentage cross-reactivity is defined as the ratio of IC$_{50}$ for racemic ractopamine to that of the test compound times 100.
[c]Clenbuterol and salbutamol did not produce competition curves.

TABLE 2

Intra- and inter-assay variations for the determination of racemic ractopamine spiked into diluted (1:10) urine.

| Spike level (ng/ml) | Found | Percentage recovery | Percent CV |
|---|---|---|---|
| Inter-assay variations (n = 5) | | | |
| 1 | 1.1 ± 0.4 | 110 | 38 |
| 5 | 3.9 ± 0.6 | 78 | 16 |
| 10 | 9.5 ± 1.7 | 95 | 18 |
| 20 | 22.4 ± 5.6 | 112 | 25 |
| Intra-assay variations (n = 12) | | | |
| 1 | 1.2 ± 0.06 | 120 | 4.6 |
| 5 | 4.2 ± 0.2 | 84 | 4.8 |
| 10 | 10.4 ± 0.6 | 104 | 5.8 |
| 20 | 20.6 ± 0.7 | 103 | 3.2 |

We claim:

1. A hybridoma cell line ATCC PTA-2103 (5G10) which produces and secretes a monoclonal antibody that binds ractopamine.

2. A monoclonal antibody produced by the hybridoma cell line of claim 1, or a fragment of said monoclonal antibody that binds ractopamine.

3. A method for detecting ractopamine in a sample comprising subjecting said sample to an immunosorbent assay comprising the steps:
   a. incubating said sample with the monoclonal antibody or monoclonal antibody fragment of claim 2 to produce ractopamine bound to said antibody or antibody fragment; and
   b. detecting said bound ractopamine.

4. The method of claim 3 wherein said sample is selected from the group consisting of animal tissue, animal excreta, human tissue, human excreta and feed material.

5. The method of claim 3, wherein said sample is of human origin and is selected from the group consisting of urine, blood, serum, plasma and hair.

6. A kit for detecting ractopamine in a sample comprising the monoclonal antibody or monoclonal antibody fragment of claim 2 and a reagent for detecting said antibody or antibody fragment.

7. A column for isolation of ractopamine or a ractopamine metabolite comprising the monoclonal antibody or monoclonal antibody fragment of claim 2 bound to a substrate in said column.

* * * * *